(12) United States Patent
Williams

(10) Patent No.: US 7,506,927 B1
(45) Date of Patent: Mar. 24, 2009

(54) AROMATHERAPY CHAIR FOR NATURAL BODILY RELAXATION, REJUVENATION AND HEALING

(76) Inventor: Angeline Kinlaw Williams, 1719 14th Street Pl., Junction City, KS (US) 66441

( * ) Notice: Subject to any disclaimer, the term of this patent is extended or adjusted under 35 U.S.C. 154(b) by 0 days.

(21) Appl. No.: 12/002,851

(22) Filed: Dec. 20, 2007

(51) Int. Cl.
*A47C 7/74* (2006.01)
(52) U.S. Cl. .................... 297/217.3; 297/464; 297/466; 297/180.12; 607/111; 607/112
(58) Field of Classification Search ............. 297/217.1, 297/217.3, 219.1, 219.12, 464, 466, 180.12; 601/49, 86, 91, 98; 607/96, 98, 108–114
See application file for complete search history.

(56) References Cited

U.S. PATENT DOCUMENTS

| | | | | |
|---|---|---|---|---|
| 82,056 | A * | 9/1868 | Wroe | 297/302.4 |
| 2,611,363 | A * | 9/1952 | Peters | 5/603 |
| 3,218,103 | A * | 11/1965 | Boyce | 297/466 |
| 3,621,191 | A | 11/1971 | Cornwell | |
| 3,644,705 | A | 2/1972 | Johnson | |
| 4,061,898 | A | 12/1977 | Murray | |
| 5,000,176 | A | 3/1991 | Daniel | |
| 5,378,042 | A * | 1/1995 | Daneshvar | 297/393 |
| 5,387,178 | A * | 2/1995 | Moses | 600/27 |
| 5,476,492 | A | 12/1995 | Unrug | |
| 5,603,728 | A | 2/1997 | Pachys | |
| 5,781,946 | A * | 7/1998 | McEntire et al. | 5/482 |
| 5,785,716 | A * | 7/1998 | Bayron et al. | 607/108 |
| 5,976,547 | A | 11/1999 | Archer | |
| 6,440,159 | B1 | 8/2002 | Edwards | |
| 6,699,271 | B2 | 3/2004 | Clayton | |
| 6,764,134 | B1 * | 7/2004 | Crescenzi et al. | 297/219.12 |
| 2003/0139693 | A1 * | 7/2003 | Swift | 601/15 |
| 2003/0173803 | A1 * | 9/2003 | Kim | 297/180.1 |

* cited by examiner

*Primary Examiner*—Peter R. Brown
(74) *Attorney, Agent, or Firm*—Theresa M. Seal

(57) ABSTRACT

An aromatherapy chair for providing natural relaxation, rejuvenation and healing for the individual's mind, body, and soul by heating herbal ingredients placed in proximity to various parts, areas, regions, and limbs of the individual's body includes an eye and sinus coverings, a pair of neck and shoulder wraps, a pair of elbow and hand therapy gloves, a back therapy pad, a pair of knee, leg, and foot boots, and a pair of thigh wraps into which the herbal ingredients are disposed and through which wiring extends for heating the herbal ingredients for relaxing and healing the areas and limbs that are covered by and inserted and enclosed within the various coverings, pads and wraps with regular house current and batteries providing energy to a thermal heating element that regulates and conducts heat to and through the wiring and the type of herbal ingredients being specific to each particular area, region, appendage or limb to be relaxed and healed.

5 Claims, 4 Drawing Sheets

AROMATHERAPY CHAIR FOR NATURAL BODILY RELAXATION, REJUVENATION AND HEALING

FIELD OF THE INVENTION

The present invention pertains to health aid products and devices, and more particularly pertains to a heated chair having herbal ingredients dispersed therethrough for the relaxation and healing of the body, mind, and soul.

BACKGROUND OF THE INVENTION

Various types of devices are commonly and widely used to relieve, relax, rejuvenate and heal areas, parts, appendages and limbs of the body. Many of these devices include the added benefit of also healing the mind and soul. Such devices can range from simple and common ice packs, heat packs, and plug-in heating pads to more exotic and expensive contrivances that can include saunas, whirlpools, warm spring baths, and reposing on heated rocks. However, all of the aforementioned devices and contrivances have their specific shortcomings from difficulty of keeping ice packs and heat packs in contact with the body portion to the expense of using saunas and whirlpools for joint, muscle and limb healing. Therapeutic wraps are a preferred healing device as they are generally portable and inexpensive, and the prior art discloses a range of therapeutic wraps.

For example, the Cornwell patent (U.S. Pat. No. 3,621,191) discloses electrically heated (low voltage) footwear and hand wear wherein an insulating layer encloses a long-stranded heating wire for heating the item to a comfortable temperature.

The Johnson patent (U.S. Pat. No. 3,644,705) discloses a low-voltage, electrically heated shirt that includes a detachable heater assembly and stretchable bands that draw the heated shirt closer to the wearer's body.

The Murray et al. patent (U.S. Pat. No. 4,061,898) discloses a heating cap for hairstyles that includes a flexible heating element sandwiched between two flexible dielectric sheets so that selected heat distribution can be applied to the cap and thus the hair.

The Daniel patent (U.S. Pat. No. 5,000,176) discloses a therapeutic wrap that includes a cross-shaped member that is wrapped about a hot or a cold pack for holding the pack in proximity to the area of the individual's body.

The Unrug patent (U.S. Pat. No. 5,476,492) discloses a body warmer for enhancing the production of body heat by the distribution of mustard herbs in the shell of a body warmer.

The Pachys patent (U.S. Pat. No. 5,603,728) discloses a scalp cooling/apparatus that includes a source of fluid for the cap, a power supply, and a thermostatic control apparatus.

The Archer et al. patent (U.S. Pat. No. 5,976,547) discloses compositions and wraps that pertain to over-the-counter analgesics and antipholigistic substances for reducing central and peripheral body inflammation and pain.

The Edwards et al. patent (U.S. Pat. No. 6,440,159 B1) discloses a multiuse therapy wrap that comprises a closed-cell neoprene laminate that is elastically deformable for fitting about various parts or portions of the body such as the ankle, calf, knee, arm, and elbow.

The Clayton patent (U.S. Pat. No. 6,699,271 B2) discloses a therapeutic wrap that can be applied to various portions of the individual's body such as the neck and shoulders.

Nonetheless, despite the ingenuity of the above devices there remains a need for an all-in-one device, such as a chair, that incorporates herbal ingredients, thermal heating elements, and wraps or pads incorporating the herbal ingredients and the thermal heating elements for providing body, mind, and soul relaxation and healing by having the wraps and extensions placed on or enclosing portions or parts of the body of the individual so that the herbal ingredients can be heated for commencing the healing process.

SUMMARY OF THE INVENTION

The present invention comprehends an aromatherapy chair that provides relaxation, rejuvenation and healing for the mind, body, and soul of the individual seated on the chair. The relaxation, rejuvenation, and healing is provided through various extensions, wraps, and pads that are placed upon, wrapped around or receive therein parts, portions, appendages or limbs of the individual seated on the chair so that herbal ingredients dispersed or distributed throughout the extensions, wraps, and pads can be warmed by electrical conductors extending therethrough and whose heating causes the release of the salutary chemical compositions and substances from the herbal ingredients thereby inducing the relaxation and healing of the individual's mind, body, and soul.

Thus, the aromatherapy chair of the present invention includes a chair having legs, a seat rest, an inclined seat back, and an inclined leg and foot support portion. A pair of arms are attached to the opposed sides of the seat back and forwardly extend toward the inclined leg and foot support portion. A detachable storage case is secured to the seat rest for storing therein a sinus covering that provides aromatherapy for the sinus and nasal regions and an eye covering that provides aromatherapy for the eyes. A housing is located beneath the seat rest and includes a control panel. The control panel includes a primary on/off button and control buttons for selectively activating each of the specific aromatherapy extensions, wraps, pads, and coverings. Circuitry and a thermal heating element are also enclosed within the housing and are interconnected to the buttons on the control panel. Electrical wiring leads out from the housing, and extends to and throughout all of the extensions, coverings, wraps, and pads for heating the herbal ingredients located and dispersed therein. A standard electrical plug for plugging into a house outlet provides power in the form of standard house electrical current to the thermal heating element while the heat for the eye covering and the sinus covering are produced by batteries placed within a battery compartment that is also contained within the housing for the control panel.

Each of the aromatherapy wraps and pads is controlled through its own on/off button so that all of the wraps and pads don't need activated if the individual only wants to use a specific wrap or pad, for example, one or both of the neck and shoulder wraps and the back therapy wrap. The material that the extensions, coverings, wraps, and pads are composed of should provide a soft touch to the skin and is preferably of the material referred to by the generic designation as terry cloth. In addition, the natural herbal ingredients for each body portion or area, for each limb, and for the eyes, sinus area, neck and shoulders are specific for that body part, portion, or area.

It is an objective of the present invention to provide an aromatherapy chair that provides for the relaxation, rejuvenation, and healing of the mind, body, and soul of the individual.

It is another objective of the present invention to provide an aromatherapy chair that helps to rid the body of pain, assists in stimulating circulation and in breaking down the toxins that accumulate in the joints and muscles.

It is still another objective of the present invention to provide an aromatherapy chair that relaxes and alleviates respiratory illnesses.

It is still yet another objective of the present invention to provide an aromatherapy chair that is able to calm, relax, and reduce mental fatigue and that can stimulate and strengthen circulation.

It is still yet a further objective of the present invention to provide an aromatherapy chair that is able to reduce and eliminate pain while offering a natural sedation.

Still yet another objective of the present invention is to provide an aromatherapy chair in which various herbal ingredients are heated to soothe and heal different parts of the body.

These and other objects, features, and advantages will become apparent upon a perusal of the following detailed description when read in conjunction with the accompanying drawing figures and appended claims.

DETAILED DESCRIPTION OF THE PREFERRED EMBODIMENT

Figure 1:
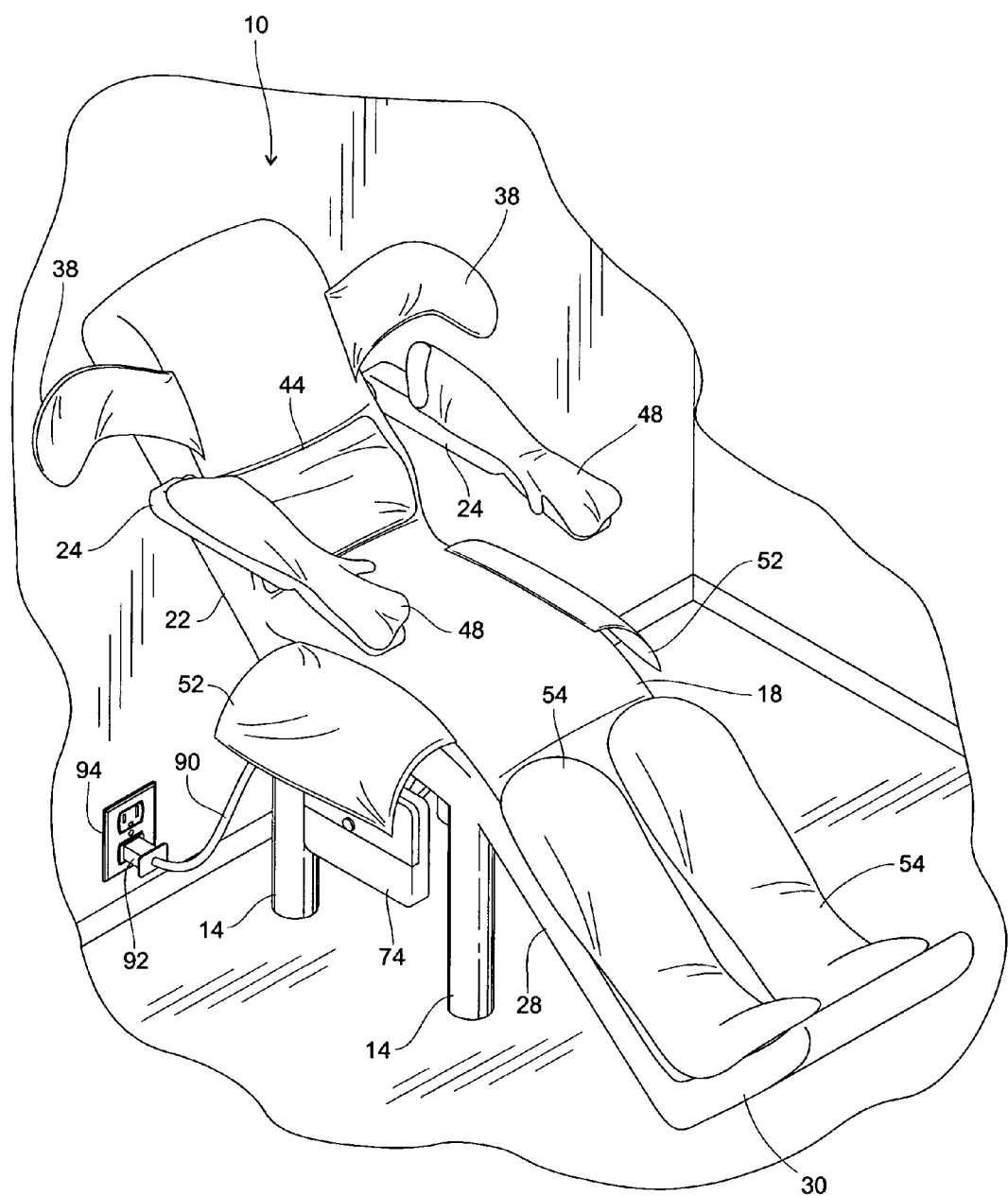
FIG. 1 is a perspective view of the aromatherapy chair of the present invention illustrating the various pads and wraps that are placed on or encompass portions or parts of the body for providing herbal relaxation and healing.

Illustrated in FIGS. 1-6 is an aromatherapy chair 10 for providing healing, relaxation, and rejuvenation to the mind, body, and soul of an individual 12 seated therein. The aromatherapy chair 10 of the present invention provides natural herbal healing for the mental and physical components or aspects of the individual 12. The aromatherapy chair 10 is portable and can be easily adapted for situations that include, but are not limited to, home uses, office uses (executive, secretary, office personnel), doctors and chiropractors' offices, sports training facilities and complexes, personal trainers, SPA's, and massage salons, rehabilitation centers, senior citizens homes, lodgings and cabins used for hikers, skiers, hunters, backpackers, etc., and daycare centers, schools and colleges.

Thus, as shown in FIGS. 1-6, the aromatherapy chair 10 includes a plurality of spaced-apart legs 14 that are attached at their respective upper ends to an underside 16 of a seat rest 18. The seat rest 18 also includes a padded and cushioned upper side 20. Upwardly extending at an angle from the seat rest 18 is a seat back 22. The back 22 of the chair 10 can be adjustable so that the individual 12 can obtain the proper inclination when situated upon the chair 10. Secured to opposed sides of the back 22 of the chair 10 are a pair of arms 24. The arms 24 can also be adjustable so that the individual 12 can comfortably rest his/her arms 26 on the arms 24. Attached to the front of the seat rest 18, and extending downwardly therefrom, is a leg support portion 28. Integrally attached to the distal end of the leg support portion 28, and projecting at a right angle therefrom, is a foot rest portion 30 for supporting the feet 32 of the individual 12 so that the individual's feet 32 don't have to dangle from the end of the leg support portion 28.

Figure 2:
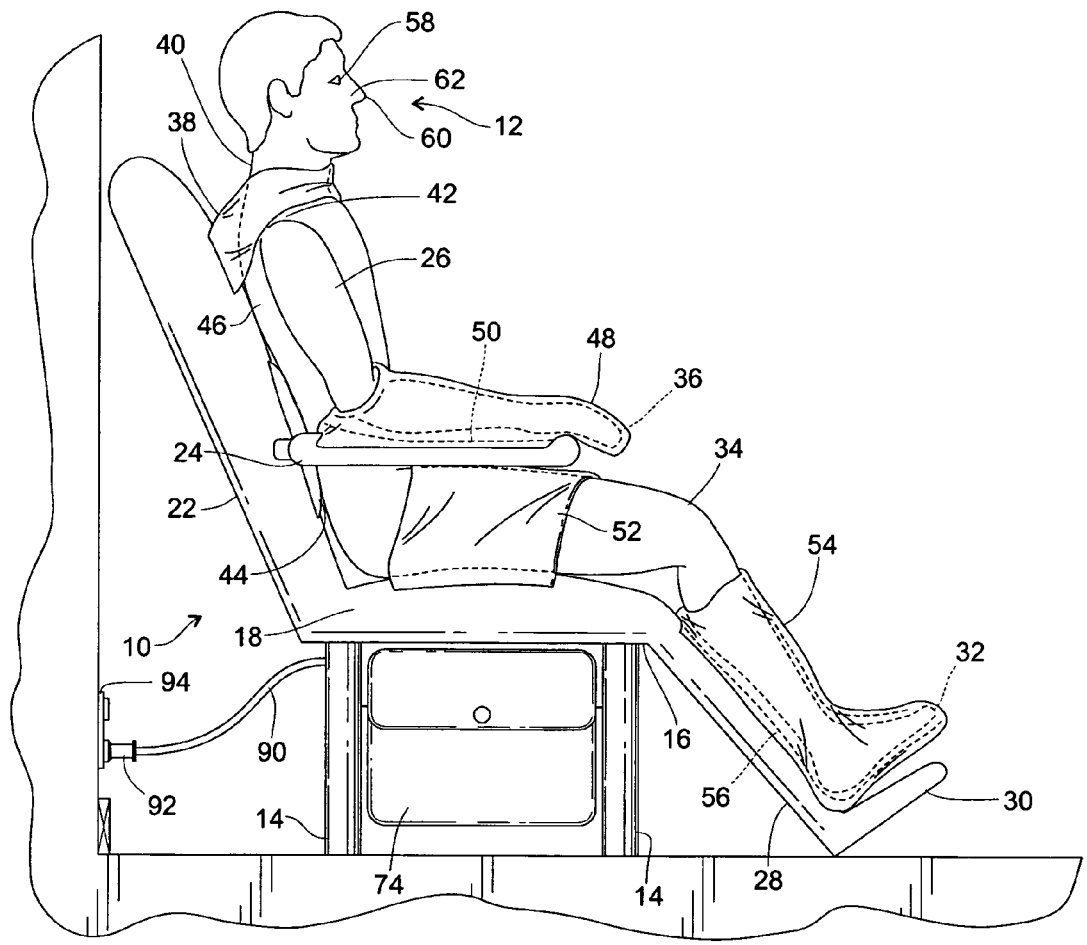
FIG. 2 is a side elevational view of the aromatherapy chair of the present invention illustrating an individual seated on the chair with the pads and wraps placed on various areas of the individual's body and with the individual's limbs placed within the extensions for herbal relaxation and healing.
Figure 4:
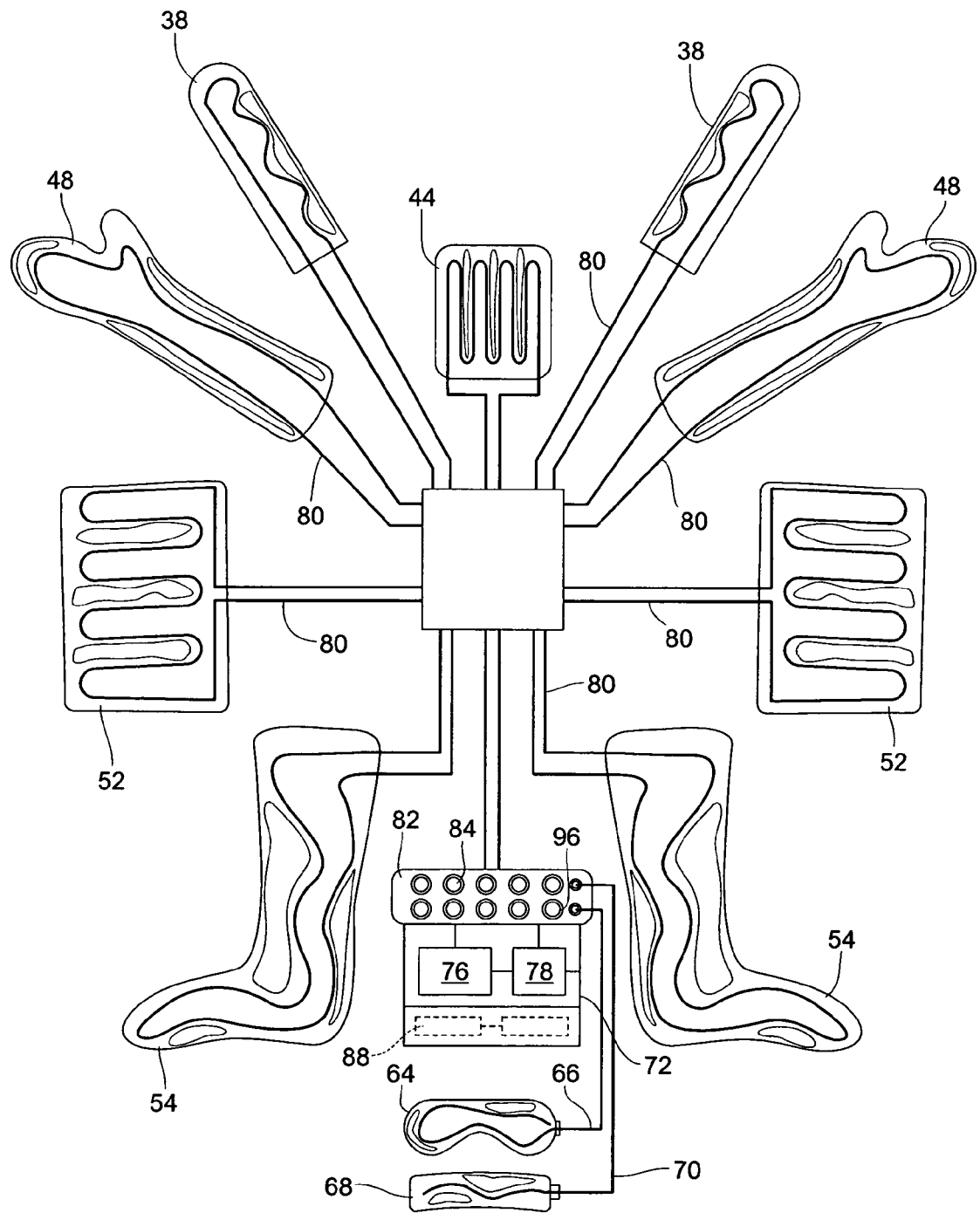
FIG. 4 is a schematic view of the aromatherapy chair of the present invention illustrating the control panel and buttons, battery compartment, the thermal heating element, and the extension of the electrical wiring throughout all the various pads and wraps.

The aromatherapy chair 10 includes a number of extensions, coverings, wraps, and pads that are integrally attached to the various portions of the chair 10 and which can be selectively wrapped about, placed or laid upon, or into which the feet 32, legs 34, hands 36, and arms 26 of the individual 12 can be inserted for receiving the aromatherapy treatment. Thus, as shown in FIGS. 1, 2 and 4, the aromatherapy chair 12 includes a pair of flexible neck and shoulder wraps 38 that are individually placeable upon the neck 40 and shoulders 42 of the individual 12 and which are interconnected adjacent the opposed sides of the back 22 of the chair 12. A back therapy pad 44 is secured to and located on the inside surface of the back 22 of the chair 10. The back therapy pad 44 is layered within the back 22 of the chair 10 and provides aromatherapy for the back 46 of the individual 12.

Illustrated in FIGS. 1, 2, and 4 are a pair of elbow and hand therapy gloves 48 with each glove 48 mounted upon the upper side of the respective arm 24 of the chair 10. Each glove 48 includes an internal cavity 50 into which the hands 36 and arms 26—up to the elbows—of the individual 12 are removably insertable for receiving the aromatherapy treatment. Attached to each opposed side of the seat rest 18 of the chair 10 is a flexible, rectangular-shaped thigh wrap 52. Each thigh wrap 52 can be placed upon and wrapped around the thigh area of the leg 34 of the seated individual 12 for providing aromatherapy treatment to that region. Mounted to the upper sides of the leg support portion 28 and the footrest support portion 30 is a pair of side-by-side knee, leg, and feet therapy boots 54. Each boot 54 generally follows the shape and contour of the leg support and foot support portion 28 and 30, and each boot 54 further includes an internal chamber 56 into which the feet 32 and legs 34 of the individual 12 (up to the knee area) can be slipped into and out of for receiving the aromatherapy treatment.

Figure 5:
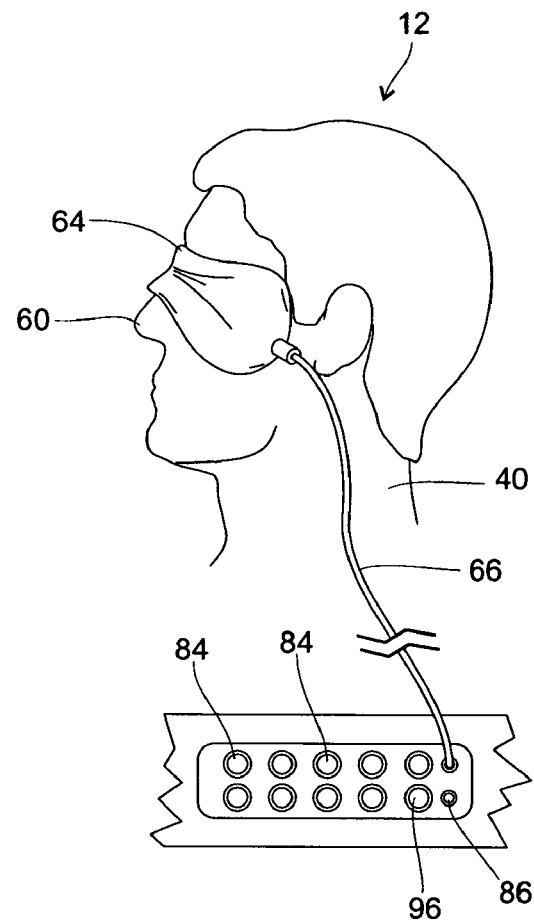
FIG. 5 is an enlarged sectioned view of the aromatherapy chair of the present invention illustrating the disposition of the herbal eye covering upon the eyes of the individual and its connection to the control panel.
Figure 6:
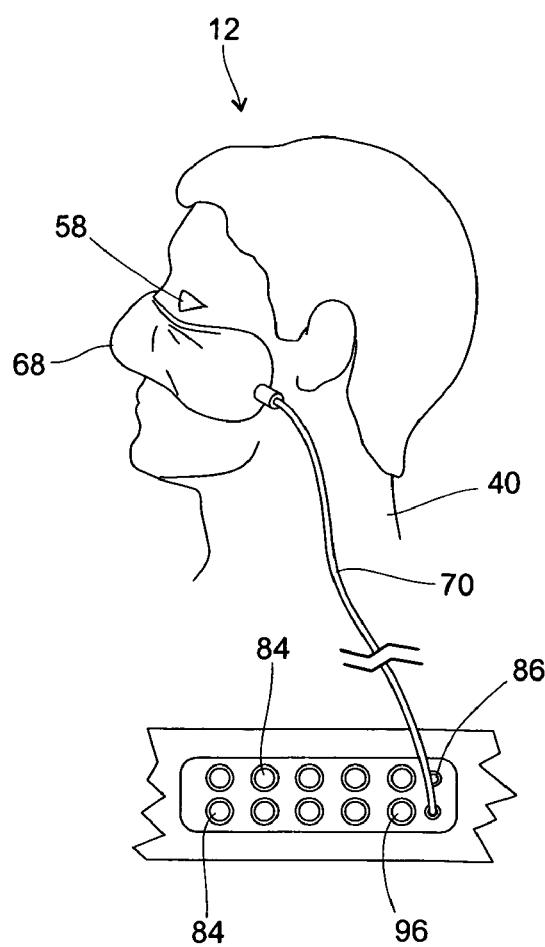
FIG. 6 is an enlarged sectioned view of the aromatherapy chair of the present invention illustrating the disposition of the herbal sinus covering upon the nose and sinuses of the individual and its connection to the control panel.

As shown in FIGS. 4-6, the aromatherapy chair 10 also includes aromatherapy pads for the eyes 58, the nose 60, and the sinus area or region 62. Specifically, a flexible eye therapy covering 64 is placed upon and over the eyes 58 of the individual 12. The eye therapy covering 64 includes an electrical wire 66 having a plug or jack at the wire's 64 distal end for plugging into and unplugging from structure hereinafter further described. In addition, the aromatherapy chair 10 also includes a flexible sinus therapy covering 68 for placement upon and over the nose 60 and sinus areas 62 of the individual 12. The sinus therapy covering 68 includes an electrical wire 70 for plugging into and unplugging from structure hereinafter further described. The sinus covering 68 and the eye covering 64 are thus attachable and detachable plug-in aromatherapy devices.

Figure 3:
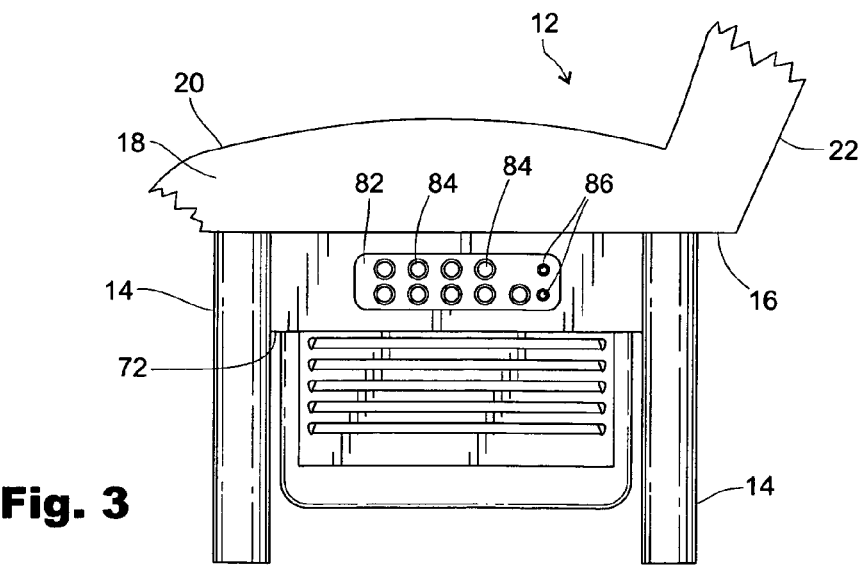
FIG. 3 is an enlarged side elevational view of the aromatherapy chair of the present invention illustrating the control buttons and the housing for the chair.

As shown in FIGS. 1-3, a housing 72 and a storage case 74 are mounted beneath the seat rest 18 of the chair 10. The sinus therapy covering 68 and the eye therapy covering 64, along with their attached electrical wires 66 and 70, can be stored within the storage case 74 when not in use. The housing 72 contains the heating, control and circuitry elements and features for the aromatherapy chair 10. Thus, enclosed within the housing 72 are the circuitry elements 76 that include a microprocessor that is electrically interconnected to a thermal heating element 78 of any standard and conventional design. Interconnected to the thermal heating element 78 and extending from the housing 72 to all the wraps, coverings and pads is electrical wiring or conductors 80 for carrying the electrical current that heats the wraps and pads for inducing the aromatherapy treatment. The thermal heating element 78 regulates the amount of heat—voltage—conveyed to the various wraps and pads by the electrical conductors 80 and which are shown in FIG. 4 as extending throughout all the pads and wraps 38, 44, 48, 52, and 54. A control panel 82 is located on the housing 72 and includes control buttons 84 hereinafter further described and a pair of jacks 86 for the plugs at the distal end of the electrical wires 66 and 70 for the sinus therapy covering 68 and the eye therapy covering 64. A battery compartment 88 for the placement therein of batteries is also contained within the housing 72 as the heat for inducing the aromatherapy treatment for the sinus therapy covering 68 and the eye therapy covering 64 is produced from batteries, and not generated from electrical current. An electrical wire 90 having a plug 92 at its distal end thereof extends from the housing 72 for plugging into a standard wall outlet or receptacle 94 so that power can be provided to the control panel 82, the thermal heating element 78, and thence to the electrical wiring or conductors 80 extending to and throughout all of the wraps, coverings, pads, gloves, and boots.

In obtain to achieve a selective use of the aromatherapy pads, gloves, boots, coverings and wraps 38, 44, 48, 52, 54, 64 and 68, as the individual 12 may only desire to use one or several pads or wraps during any given therapy session, i.e., only the knee, leg, and feet therapy boots 54 to treat and heal a sore or strained calf or thigh, the control buttons 84 are further designated as individual wrap and pad control buttons mounted on the control panel 82 of the housing 72 as well as a primary on/off button 96 for initially activating the aromatherapy chair 10 after the chair 10 has been plugged into the wall outlet 94. Thus, the control button 84 designated button one activates the neck and shoulder wraps 38, button two activates the back therapy pad 44, button three activates the elbow and hand therapy gloves 48, button four activates the thigh wraps 52, button five activates the knee, leg, and feet boots 54, button six activates the eye therapy covering 64, and button seven activates the sinus therapy covering 68. The control buttons 84 denoted one, three, four, and five can be further designed so that pressing these buttons once activates the left-hand wrap, glove, or boot 38, 48, 52, or 54, while pressing the aforesaid control buttons twice activates the right-hand wrap, glove, or boot 38, 48, 52, or 54. This provides an even more selective use of the aromatherapy chair 10 for targeting and treating specific areas of the body.

The aromatherapy chair 10 includes a wide range of herbal substances, compounds, or ingredients 98 for producing the natural body relaxation and healing, and the components of the chair 10—the wraps, pads, coverings, mitts, and boots 38, 44, 48, 52, 54, 64, and 68—are filled with or have disposed or permeated therein the herbal ingredients 98. Moreover, specific herbal ingredients are designated for each area of the body and thus unique ingredients are placed or located in the various wraps, coverings, pads, and mitts.

Thus, the herbal ingredients 98 disposed or located in the neck and shoulder wraps 38, the back therapy pad 44, the elbow and hand therapy gloves 48, the thigh wraps 52, and the knee, leg, and feet therapy boots 54 are selected from the range of herbal ingredients 98 that include the following: allspice which is a natural sedative for relaxation; black pepper for stimulating circulation; ginger for easing joint pain; juniper berry that relaxes muscle spasms; and mustard seed for stimulating circulation for breaking down toxins in the muscles and joints. The eye therapy covering 64 and the sinus therapy covering 68 have placed or disposed therein herbal ingredients 98 selected from a range that includes the following: basil for treating respiratory ills and which is also a mentally clarifying antispasmodic; marjoram for easing respiration and which is an analgesic and sedative; peppermint for cooling, soothing and use as a decongestant; rosemary which is an analgesic, relaxant, for reducing mental fatigue; increasing circulation, and easing headaches; chamomile for soothing, calming, and promoting a "dream" state of mind, and which is also an anti-inflammatory; and lavender for producing sweetness, calming, soothing, and balancing emotions and thoughts, and which is an analgesic and an anti-depressant.

Thus, the aromatherapy chair 10 is an all-in-one device for treating the mind, body, and soul of the individual 12 by selectively placing one or more of the wraps, boots, gloves, and coverings 38, 42, 44, 48, 52, 54, 64, and 68 upon the various regions of the body or by the individual 12 placing his or her arms 26 and legs 34 into the gloves and boots 48 and 54. The aforesaid devices can be selectively turned on as needed via the respective control buttons 84 so that heat is conveyed and transferred from the thermal heating element 78 in a regulated manner through the electrical wiring 80 extending through all the wraps, pads, coverings thereby causing the release of the active healing and relaxing substances and compounds of the specific herbal ingredients 98.

The described embodiments of the aforesaid invention are to be considered in all respects only as illustrative and not restrictive, and the scope of the invention is therefore indicated by the appended claims and any and all changes, variations, and alterations are considered to come within the meaning and range of the claims and are to be embraced within their scope and equivalents thereof.

I claim:

1. An aromatherapy chair for the herbal relaxation and healing of the arms, legs, hands, feet, thighs, back, neck, shoulders, eyes, and sinus areas of the individual seated thereon, comprising:
   a plurality of legs;
   a seat rest supported by the legs;
   a seat back attached to an upwardly extending from the seat rest;
   a leg support portion attached to the seat rest opposite of the seat back and downwardly extending therefrom;
   a foot support portion attached to the leg support portion;
   a pair of arms attached to the seat back and extending above the seat rest toward the leg support portion;
   a pair of neck and shoulder wraps attached to the seat back for placement upon the neck and shoulders of the individual;
   a back therapy pad secured to the seat back for herbal relaxing and healing the back of the individual;
   a pair of elbow and hand therapy gloves with one glove attached to each arm for receiving therein one arm of the individual for herbal relaxation and healing thereof;
   a pair of thigh wraps attached to the seat rest for placement upon the thighs of the individual for herbal relaxation and healing thereof;
   a pair of knee, leg, and foot therapy boots disposed on the leg support portion and into which the feet and legs of the individual are inserted for herbal relaxation and healing;

a plurality of herbal ingredients located within the neck and shoulders wrap, the back therapy pad, the gloves, the gloves, the boots, and the thigh wraps;

a housing secured to the underside of the seat rest;

a control panel mounted to the housing and including a plurality of control bottom for activating the neck and shoulder wraps, the back therapy pad, the thigh wraps, the boots and the gloves;

a thermal heating element enclosed within the housing and electrically interconnected to the control panel; and a plurality of electrical conductors interconnected to the thermal heating element and extending into the neck and shoulders wraps, the back therapy pad, the gloves, the thigh wraps, and the boots for heating the herbal ingredients disposed therein so that the individual can receive herbal relaxation and healing.

2. The aromatherapy chair of claim 1 further comprising a storage case mounted beneath the seat rest of the chair.

3. The aromatherapy chair of claim 2 further comprising a sinus therapy covering for placement upon the nose and sinus region of the individual for the herbal relaxation and healing thereof.

4. The aromatherapy chair of claim 3 further comprising an eye therapy covering for placement upon the eyes of the individual for the herbal relaxation and healing thereof.

5. An aromatherapy chair for the herbal relaxation and healing of the arms, legs, hands, feet, thighs, back, neck, shoulders, eyes, nose and sinus areas of the individual seated thereon, comprising:

a pair of neck and shoulder wraps attached to the chair for placement upon the neck and shoulders of the individual;

a back therapy pad secured to the chair for herbal relaxing and healing of the back of the individual;

a pair of elbow and hand therapy gloves attached to the chair for receiving therein the arms of the individual for the herbal relaxation and healing thereof;

a pair of thigh wraps attached to the chair for placement upon the thighs of the individual for the herbal relaxation and healing thereof;

a pair of knee, leg, and foot therapy boots secured to the chair and into which the feet and legs of the individual are inserted for the herbal relaxation and healing thereof;

a plurality of herbal ingredients located within the neck and shoulders wrap, the back therapy pad, the gloves, the thigh wraps, and the boots;

a housing secured to the underside of the seat rest of the chair;

a control panel mounted to the housing and including a plurality of control buttons for activating the neck and shoulder wraps, the back therapy pad, the thigh wraps, the gloves, and the boots;

a thermal heating element enclosed within the housing and electrically interconnected to the control panel;

a plurality of electrical conductors interconnected to the thermal housing element and extending into the neck and shoulder wraps, the back therapy pad, the gloves, the thigh wraps, and the boots for heating the herbal ingredients disposed therein so that the individual can receive herbal relaxation and healing;

a storage case mounted to and beneath the seat rest of the chair;

a sinus therapy covering for placement upon the nose and the sinus region of the individual for the herbal relaxation and healing thereof;

an eye therapy covering for placement upon the eyes of the individual for the herbal relaxation and healing thereof;

the sinus therapy covering and the eye therapy covering are placed within the storage case when not in use;

the housing including a battery compartment for the placement therein of at least two batteries; and the herbal ingredients disposed within the sinus therapy covering and the eye therapy covering are heated by the batteries.

* * * * *